United States Patent [19]

Holzinger et al.

[11] 4,043,676
[45] Aug. 23, 1977

[54] PHOTOMETER

[75] Inventors: Otto Holzinger; Wilhelm Pross, both of Munich, Germany

[73] Assignee: Carl Zeiss Stiftung, Heidenheim (Brenz), Germany

[21] Appl. No.: 597,291

[22] Filed: July 18, 1975

[30] Foreign Application Priority Data

July 25, 1974 Germany .............................. 2435908

[51] Int. Cl.$^2$ .............................................. G01J 1/44
[52] U.S. Cl. .................................................. 356/226
[58] Field of Search ............... 356/218, 223, 224, 226, 356/229, 230; 324/130; 330/9

[56] References Cited

U.S. PATENT DOCUMENTS

| 3,516,751 | 6/1970 | Fruengel | 356/226 |
| 3,784,912 | 1/1974 | Van Aken | 324/130 |
| 3,801,919 | 4/1974 | Wilkes et al. | 330/9 |

OTHER PUBLICATIONS

Jaeger, R. C. and Hellworth, G. A., "Dynamic-Zero Correction Method Suppresses Offset Error in Op Amps", Electronics, Dec. 4, 1972, pp. 109–110.

Primary Examiner—John K. Corbin
Assistant Examiner—Rolf Hille
Attorney, Agent, or Firm—Blanchard, Flynn, Thiel, Boutell & Tanis

[57] ABSTRACT

A photometer for measuring the light transparency of a substance. A light beam is provided for illuminating a substance, which light beam passes through the substance and strikes a photoelement and produces a measuring current. The voltage generated from the measuring current is logarithmated by a converter circuit and is supplied to an indicating instrument for indicating a measured value. A zero balance control circuit is provided for controlling the voltage applied to the indicating instrument so that the indicating instrument will return to a value determined by a previous measuring of a calibrated substance. If the transparency of the measured substance is identical to the transparency of the calibrated substance, the indicating device will return to a zero value. A value other than zero will indicate the difference in transparency of the measured substance from the calibrated substance.

6 Claims, 2 Drawing Figures

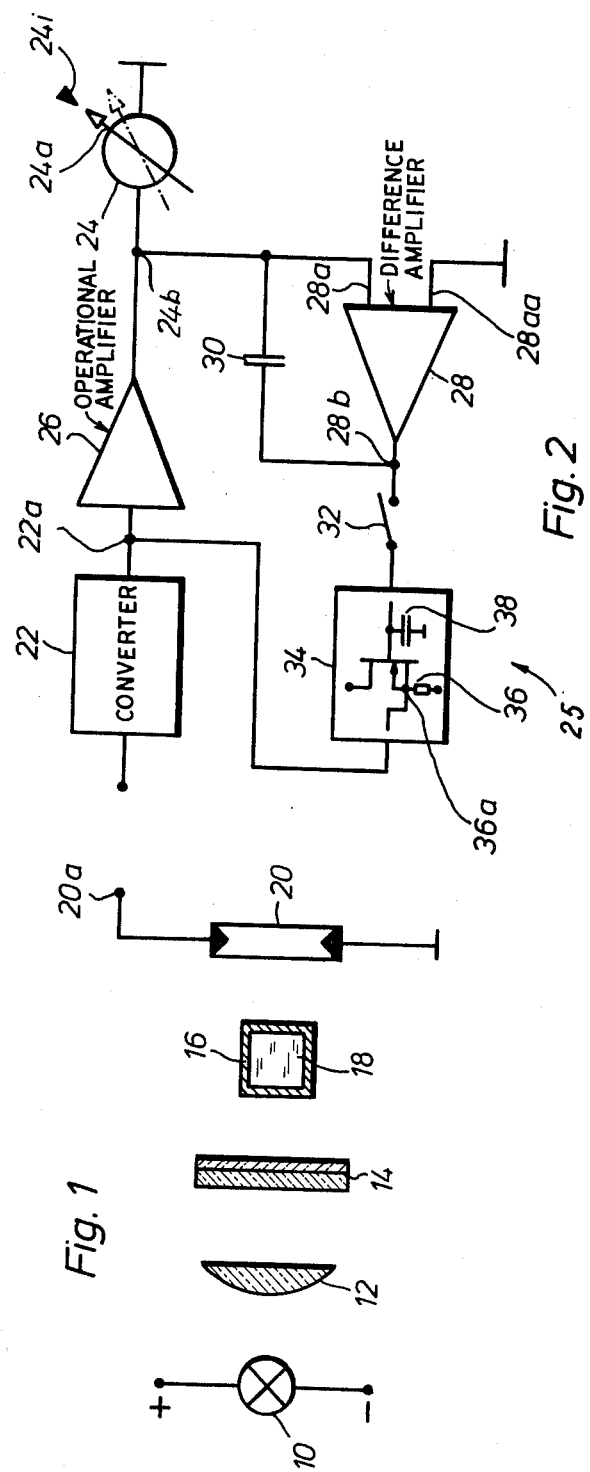

PHOTOMETER

FIELD OF THE INVENTION

The invention relates to a photometer for measuring the transparency of a substance, wherein a light beam, after an illuminating of this substance, strikes a photoelement and produces a measuring current, the voltage of which, which corresponds to the transparency of the substance (transmission), is logarithmated by means of a converter and is indicated as a measured value (extinction) on an indicating instrument, and wherein an electronic control circuit is provided, which operates after operation of a switch and controls the voltage applied on the indicating instrument to a zero value (extinction = 0).

BACKGROUND OF THE INVENTION

A zero balance procedure is carried out in such devices usually for correction purposes to eliminate measuring differences which have been caused by variable factors, for example, lamp brightness, photoelement sensitivity and others. However, where measurements are performed as relative measurements (measuring substance in reference to a calibration substance), such a zero balance is necessary in the case of the calibration substance measurement, in order to be able to read off directly at the indicating instrument the looked-for difference value when the transparency of the actual substance is measured.

In the case of known photometers, a control member which can in most cases be adjusted manually by, for example a potentiometer or an element operating as a multiplier or divider, for example a photomultiplier tube is used for the zero balance procedure, both of which are arranged in the circuit before the logarithmic converter. However, this known control arrangement requires, in order to offer a sufficient control, expensive and complicated electronic circuitry, which considerably increases the purchasing expenses of this device.

It is now the purpose of the present invention to overcome this disadvantage and to accomplish the zero balance procedure of the photometer by electronic measures, which zero balance can be accomplished with a substantially more economical input and, in spite of this, assures a wider linear control range. This purpose is attained according to the invention, so that an element which acts as an addition or substaction circuit is connected in circuit with and between a converter and an indicating instrument and a control circuit, functioning as the zero balance circuit, is connected at the output of the converter.

In the preferred embodiment of the invention, an operational amplifier functions as an addition or subtraction circuit. The control circuit includes therein a difference amplifier which is connected to function as an integrator circuit, a capacitor storing the integrated voltage, a reed contact serving as a switch and a storage circuit.

According to a further characteristic of the invention, the storage circuit includes a capacitor and a FET (field effect transistor). The aforementioned storage circuit will function so that after a reopening of the reed contact, the zero balance is maintained over a certain time span.

In the case of devices which measure the transparency of a substance and which must be inspected, the measured value of the device is compared with the measured value of a calibration substance to indicate the difference amount at the indicating instrument and the calibration substance can be measured during a simultaneous zero balance prior to each measuring of the substance which is to be examined. However, it is also possible, after measuring the calibration substance, to conduct, with a single zero balance procedure, a subsequent series of substance measurments, in as far as this series of measurements can be conducted within the time duration of the storage circuit action.

BRIEF DESCRIPTION OF THE DRAWING

One exemplary embodiment of the invention will be discussed more in detail in the following description with reference to the drawing, in which:

FIG. 1 is a schematic illustration of the optic mechanical part of a photometer, and FIG. 2 is a block diagram of the associated electric circuit.

DETAILED DESCRIPTION

FIG. 1 illustrates the important mechanical-optical elements of a conventional single-beam photometer, namely a lamp 10 for producing a light beam, a field lens 12, if desired, a movable filter 14, and a cell 16, which is filled with a light transparent substance 18. The lamp 10 is connected to a current source, preferably to a current source which supplies also the operating voltage for the herein-after discussed measuring circuit by means of a not illustrated switch connection. A photoelement 20 is arranged in the path of the beam of the photometer following the cell 16, which photoelement produces a measuring current when loaded by the light beam, the voltage (transmission) of the measuring current being proportional to the light transmission characteristic of the substance 18. The voltage which is obtained at the output 20a of the photoelement 20 is amplified in a suitable manner and is fed as an input voltage signal to the measuring circuit illustrated in FIG. 2.

The measuring circuit includes a converter 22, which operates linearly in the broad range and which converts the signal to the logarithm of the input voltage (transmission) and forwards same as a measured value (extinction) to the input terminal 24a of an indicating instrument 24. An operational amplifier 26 is connected between the converter 22 and the indicating instrument 24 and functions as an addition or subtraction circuit. A control circuit 25 which functions as a zero balance circuit is connected to an output terminal 22a of the converter 22. The control circuit 25 includes a series connected storage circuit 34, a high resistance reed switch 32 and a difference amplifier 28, connected to function as an integrator, connected between the output terminal 22a and the input terminal 24b. A capacitor 30 is connected between the input and output terminals 28a and 28b, respectively, of the differnce amplifier 28 to store an integrated voltage signal. A field effect transistor (FET) 36 and a capacitor 38 are arranged in the storage circuit 34.

A substance measurement takes place in such photometers in a conventional manner according to the formula ti, $E = -\log T$, wherein $E$ = extinction (in volts) and $T$ = transmission (in volts). Thus a transmission $T_1 = 1.00$ ($v$) will correspond to an extinction $E_o = 0$ ($v$). These values are in practice mostly assumed as base values for the measuring operation, because they have for example during relative measurements (measuring substance in relation to a standard substance) the advantage that one can directly read off the difference value of the two extinctions during an actual substance measurement following the standard substance measurement, of course with the condition that during the standard substance measurement a balance of the indication to zero value takes place ($E = 0$).

If after illuminating a substance, the photelemment 20 sends a voltage (transmission) signal to the converter 22, then the logarithmic voltage (extinction) will be fed to the indicating instrument 24 and will here cause a certain deflection of the indicator 24a from the zero position (at index 24a ) to, for example, the indicating position which is illustrated in a dash-dotted line in FIG. 2. The reed contact 32 is closed for the zero balance after which a voltage is integrated by the difference amplifier 28 and the capacitor 30 until the signal at both inputs 28a, 28aa of the difference amplifier 28 are at the same voltage, in the present case zero volts. The integrated voltage existing at the output 28b of the difference amplifier 28 is stored in the storage circuit 34 on the capacitor 38 which is connected to the gate of the FET 36. A voltage from a voltage divider is fed to the source connection 36a of the FET 36, which voltage is, in turn, fed to the input of the operational amplifier 26. Since this voltage which has been fed to the operational amplifier 26 from the control citcuit 25 is equal in value to the voltage effecting the deflection of the indicator 24a, however, is oppositely poled, the indicator 24a will return, after the zero balance has been effected, again to the zero position at the index 24i.

The voltage which exists at the capacitor 38 and which during the zero balance is integrated is maintained for a longer period of time also after the reopening of the reed contact 32, so that during this period of time the zero balance remains constant and the indication of $E = 0$ is maintained for a long time.

If with the aforedescribed arrangement a comparison measurement of a substance is to be conducted, first a cell 16 having a balancing substance therein is introduced into the device, is illuminated and the deflection of the indicator 24a which occurs at the indicating instrument 24 is moved back to zero value with the aid of the control circuit 25. A different cell 16 is now used, which, however, contains the substance which is to be measured. Afer illuminating this new substance, the indicator 24a will deflect, which deflection directly indicates the difference amount of the two substance extinctions.

It has already been mentioned that the zero balance is maintained over a certain time period by the capacitor 38 in the storage circuit 34. Therefore, after conducting a zero balance function, a series of substance measurements can also be conducted. Furthermore, it is possible in other cases to conduct during this time period a so-called kinetic measurement of a substance, namely one can measure the same substance at certain constant time intervals in order to determine the substance behavior pattern during the time duration.

Finally it is to be noted that a conventional instrument for range indication can be connected to the connecting line between the storage circuit 34 and the operational amplifier 26, which instrument indicates the linear measuring range of the converter 22, within which each measured value can be controlled to the zero value with the aid of the control circuit. If, during a measurement procedure, the linear range is exceeded or not reached, the amplifier adjustment at the photometer must be changed.

Although a particular preferred embodiment of the invention has been disclosed in detail for illustrative purposes, it will be recognized that variations or modifications of the disclosed apparatus, including the rearrangement of parts, lie within the scope of the present invention.

The embodiment of the invention in which an exclusive property or privilege is claimed are defined as follows:

1. A photometer having a light source for use with plural substance holding means for holding the same or different substances to facilitate a measuring of the light transparency of said substance or substances, comprising:

a photoelement having a characteristic of producing a variable signal proportional to the amount of light being received thereby and which is transmitted through a calibration substance;

converter means responsive to said signal for converting said signal to a logarithmated signal;

amplifier means responsive to said logarithmated signal for amplifying said logarithmated signal;

indicator means responsive to said amplified signal for indicating the magnitude of said amplified signal; and control circuit means connected in parallel with said amplifier means and including storage means for storing a signal equal in magnitude but opposite in polarity, to said logarithmated signal, said control circuit means further including switching means for isolating said storage means from the output of said amplifier means while simultaneously supplying said stored signal to the input to said amplifier means to cause said indicator means to indicate a zero signal value indicative of the light transparency of said calibration substance whereby a second logarithmated signal produced by said converter means for another different substance will cause said indicator means to indicate the difference between said storage signal and said second logarithmated signal and thereby the difference in light transparency between said calibration substance and said different substance.

2. A photometer according to claim 1, wherein said control circuit means includes a difference amplifier connected to function as an integrator, a capacitor for storing an integrated voltage from said difference amplifier equal in magnitude but opposite in polarity to said logarithmated signal, said switching means comprising a reed contact positioned between said difference amplifier and said capacitor.

3. A photometer according to claim 2, wherein said storage means maintains, after a reopening of said reed contact, said stored signal over a certain time span.

4. A photometer according to claim 2, wherein said control circuit means further includes a field effect transistor responsive to said stored signal for delivering said stored signal to said input to said amplifier means.

5. A photometer according to claim 1, wherein said another substance is measured in such a manner that its logarithmated value is compared with said logarithmated value of said calibration substance and wherein said calibration substance is measured to generate said zero signal value prior to each measurement of said different substance.

6. A photometer according to claim 1, wherein said another substance is measured in such a manner that its logarithmated value is compared with said logarithmated value of said calibration substance and wherein after generating a zero signal value, a series of substance measurements can occur and which can be conducted within the time duration of said storage means.

* * * * *